United States Patent [19]

Tsukada et al.

[11] Patent Number: 5,283,624
[45] Date of Patent: Feb. 1, 1994

[54] MULTI-ELEMENT SIMULTANEOUS ANALYSIS ATOMIC ABSORPTION SPECTROSCOPY PHOTOMETER AND MULTI-ELEMENT SIMULTANEOUS ANALYTIC METHOD

[75] Inventors: Masamichi Tsukada, Ibaraki; Konosuke Oishi, Mito, both of Japan

[73] Assignee: Hitachi, Ltd., Tokyo, Japan

[21] Appl. No.: 597,324

[22] Filed: Oct. 15, 1990

[30] Foreign Application Priority Data

Oct. 18, 1989 [JP] Japan .................. 1-268947

[51] Int. Cl.$^5$ .............................. G01J 3/42; G01J 3/28
[52] U.S. Cl. ......................... 356/319; 356/328
[58] Field of Search ............. 356/319, 331–334, 356/312, 311, 326–328; 422/61

[56] References Cited

U.S. PATENT DOCUMENTS

| | | | |
|---|---|---|---|
| 4,867,562 | 9/1989 | Oishi et al. | 356/312 |
| 4,992,380 | 2/1991 | Moriarty et al. | 422/62 X |

FOREIGN PATENT DOCUMENTS

| | | | |
|---|---|---|---|
| 0069220 | 4/1982 | Japan | 356/334 |
| 0111422 | 5/1982 | Japan | 356/334 |
| 0081520 | 5/1984 | Japan | 356/329 |
| 63-292040 | 1/1988 | Japan | 356/312 |
| 2131200A | 6/1984 | United Kingdom . | |

OTHER PUBLICATIONS

Retzik et al, "Concept and Design of a Simultaneous Multielement GFAAS," International Laboratory, vol. 18, #8, Oct. 1989, pp. 49–56.

Manning et al, "The Determination of Truce Elements in Natural Waters Using the Stabilized Temperature Platform Furnace," Applied Spectroscopy, vol. 37, #1, Feb. 1983, pp. 1–11.

Primary Examiner—Vincent P. McGraw
Assistant Examiner—K. P. Hantis
Attorney, Agent, or Firm—Antonelli, Terry, Stout & Kraus

[57] ABSTRACT

Incident slits and exit slits are provided separately on corresponding optical axes incident simultaneously on a spectroscope from a sample atomizing unit. A mechanism for changing the widths of the respective incident slits and exiting slits is provided such that the slit widths optimal to the respective elements to be measured are set on the corresponding optical axes to thereby realize high sensitivity analysis of all the elements to be measured simultaneously.

32 Claims, 10 Drawing Sheets

IRON SPECTRUM INCLUDING MANY NEIGHBORING LINES

FIG. 9

| ELEMENT NAME | ATOMIC ABSORPTION WAVELENGTH | NEIGHBORING LINE WAVELENGTH | SLIT WIDTH |
|---|---|---|---|
| IRON | 248.3 nm | 248.8 nm | 0.2 nm |
| COBALT | 240.7 nm | 241.1 nm | 0.2 nm |
| NICKEL | 232.0 nm | 231.6 nm | 0.2 nm |
| COPPER | 324.8 nm | — | 0.8 nm |
| ARSENIC | 193.7 nm | — | 1.3 nm |
| POTASSIUM | 766.5 nm | — | 0.8 nm |
| SODIUM | 589.0 nm | 589.6 nm | 0.4 nm |
| SELENIUM | 196.0 nm | — | 1.3 nm |
| ⋮ | ⋮ | ⋮ | ⋮ |

FIG. 10

EFFECT OF SLIT WIDTH ON IRON WORKING CURVE

FIG. 12

MULTI-ELEMENT SIMULTANEOUS ANALYSIS ATOMIC ABSORPTION SPECTROSCOPY PHOTOMETER AND MULTI-ELEMENT SIMULTANEOUS ANALYTIC METHOD

BACKGROUND OF THE INVENTION

The present invention relates to atomic absorption spectroscopy photometers and more particularly to a multi-element simultaneous analysis atomic absorption spectroscopy photometer which analyzes a plurality of elements simultaneously.

A multi-element simultaneous analysis atomic absorption spectroscopy photometer simultaneously impinges light beams from a plurality of hollow cathode lamps (light sources) including the bright lines of elements to be detected on a heating furnace (sample atomizing unit) at a fixed angle to the furnace, selects the absorption wavelengths of the light beams absorbed by the atomic vapor of a sample which occurs during heating using a spectroscope provided after the heating furnace, detects the optical intensities of the selected wavelengths using photodetector systems, and determines the multiple elements contained in the sample from the proportions of absorption by those elements. The same applicant has proposed a photometer for analyzing multiple elements simultaneously, as disclosed in Unexamined Japanese Patent Publication JP-A-63-292040.

Figure 8:
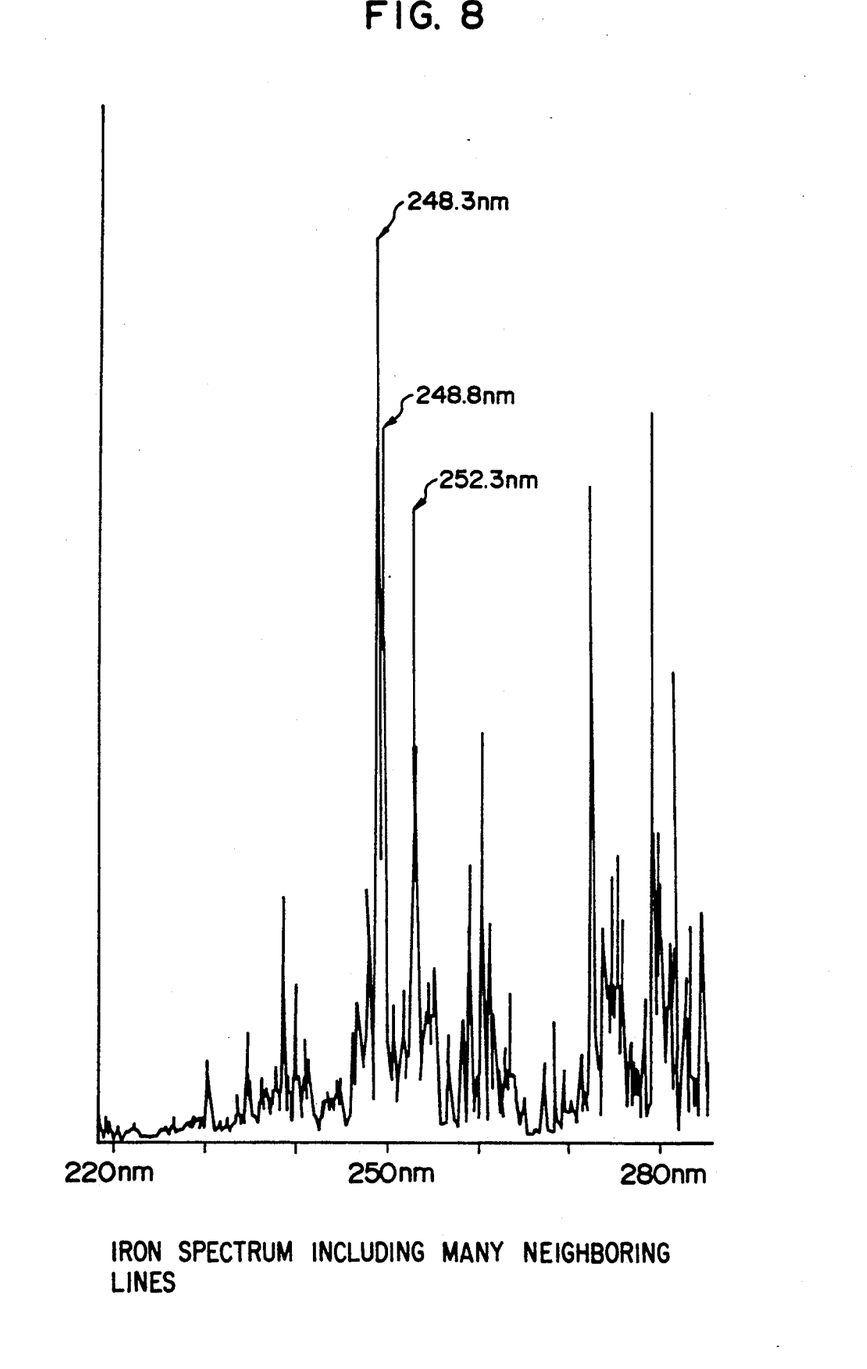
FIG. 8 illustrates the absorption spectrum of iron.
Figure 9:
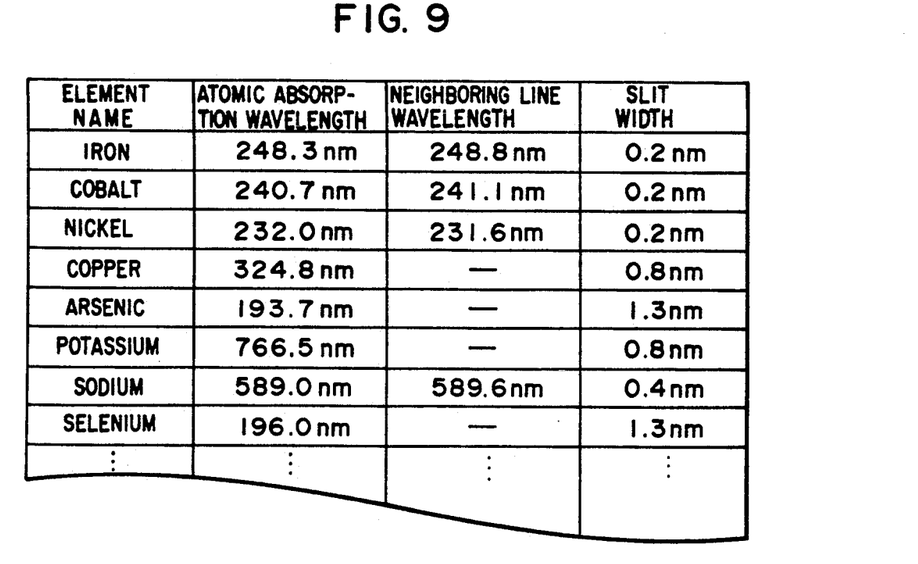
FIG. 9 is a table indicative of device conditions for elements.
Figure 10:
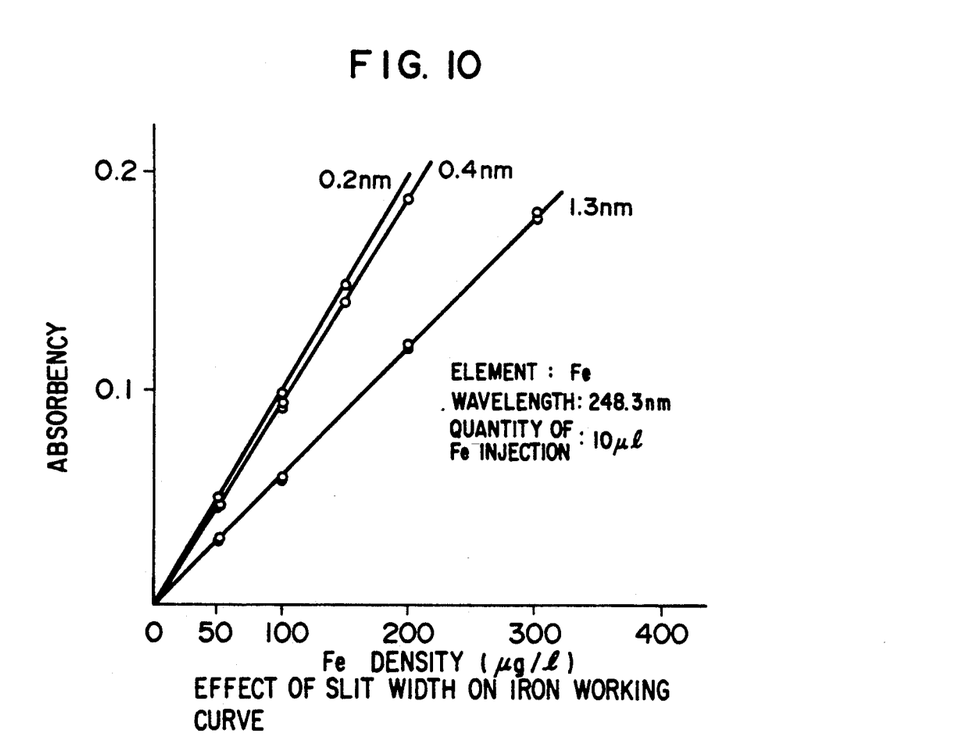
FIG. 10 illustrates a working line for iron obtained when the slit width is changed.

However, the proposed photometer has the following drawbacks:

(1) The conventional photometers disposed in the corresponding optical systems each have a single incident slit having a fixed width and a single exit slit having a fixed width, so that they each may not be suitable for an element to be measured and thus the sensitivity of the spectroscope is likely to decrease depending on that element. As the slit width becomes wider, a greater quantity of light is usually obtained, so that a higher S/N ratio signal is obtained and an electric current which lights a lamp is reduced, and the lamp service life is increased advantageously. However, as the slit width increases, a so-called atomic absorption wavelength which absorbs light most efficiently cannot be separated from a neighboring absorption wavelength (neighboring line) close thereto and the absorption sensitivity can decrease depending on an element to be measured, due to the background produced by the neighboring line. FIG. 8 illustrates the state of neighboring lines of an iron cathode lamp, and FIG. 9 illustrates an extraction of some examples of atomic absorption wavelengths of elements, the presence/absence of neighboring lines and recommended slit widths to avoid those neighboring lines. The closer the neighboring line is, the narrower the slit width should be. Since elements such as arsenic having a low melting point have low absorption efficiency, the slit width is required to increase sufficiently. FIG. 10 illustrates the effect of a slit width on an iron working curve having a neighboring line. It will be seen that as the slit width becomes narrower, the absorbency for the same density increases and the sensitivity also increases. As illustrated by the above examples, the sensitivity for some elements decreased when the spectroscope used had a single slit and the entire optical system had the same fixed slit width. For example, among the elements illustrated in Table 9, it was difficult to cope with a combination of iron and nickel for which it is desirable to reduce the slit width because they produce a neighboring line, and arsenic and selenium for which it is desirable to increase the slit width because the lamp used is dark.

Figure 11:
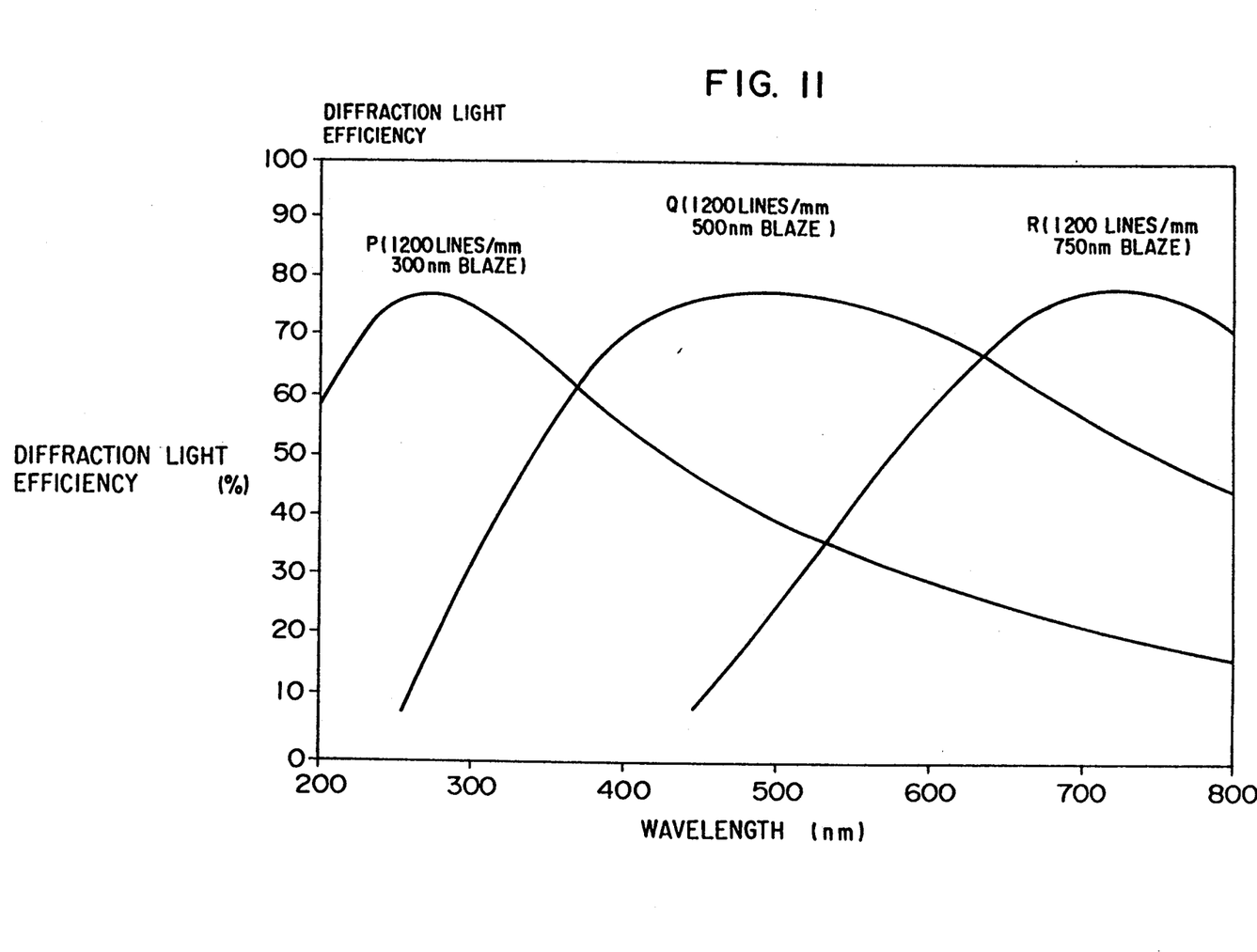
FIG. 11 illustrates the diffraction light efficiency of a diffraction grating depending on blaze wavelength.

(2) Although the respective diffraction gratings of a spectroscope are disposed independently in the corresponding optical systems, they have exactly the same specifications. Therefore, they do not match with the atomic absorption wavelength regions of some elements and do not provide sufficient sensitivities. When the reflective surface constituted by the angle of a roof-like groove constituting a diffraction grating, or a so-called blaze angle, properly faces parallel incident light beams thereon in a Littrow grating spectrograph or when a similar refractive surface of a Czerny-Turner spectrometer is between parallel incident light beams and a dispersive reflective angle, the reflective efficiency becomes maximum on the diffraction grating surface, in which this wavelength is called the "blaze wavelength". FIG. 11 illustrates how the relationship between the diffraction light efficiency and wavelength of a diffraction grating varies with blaze wavelength. If a diffraction grating having a blaze wavelength more suitable for a wavelength or element to be measured can be selected, the sensitivity will be increased greatly.

Figure 12:
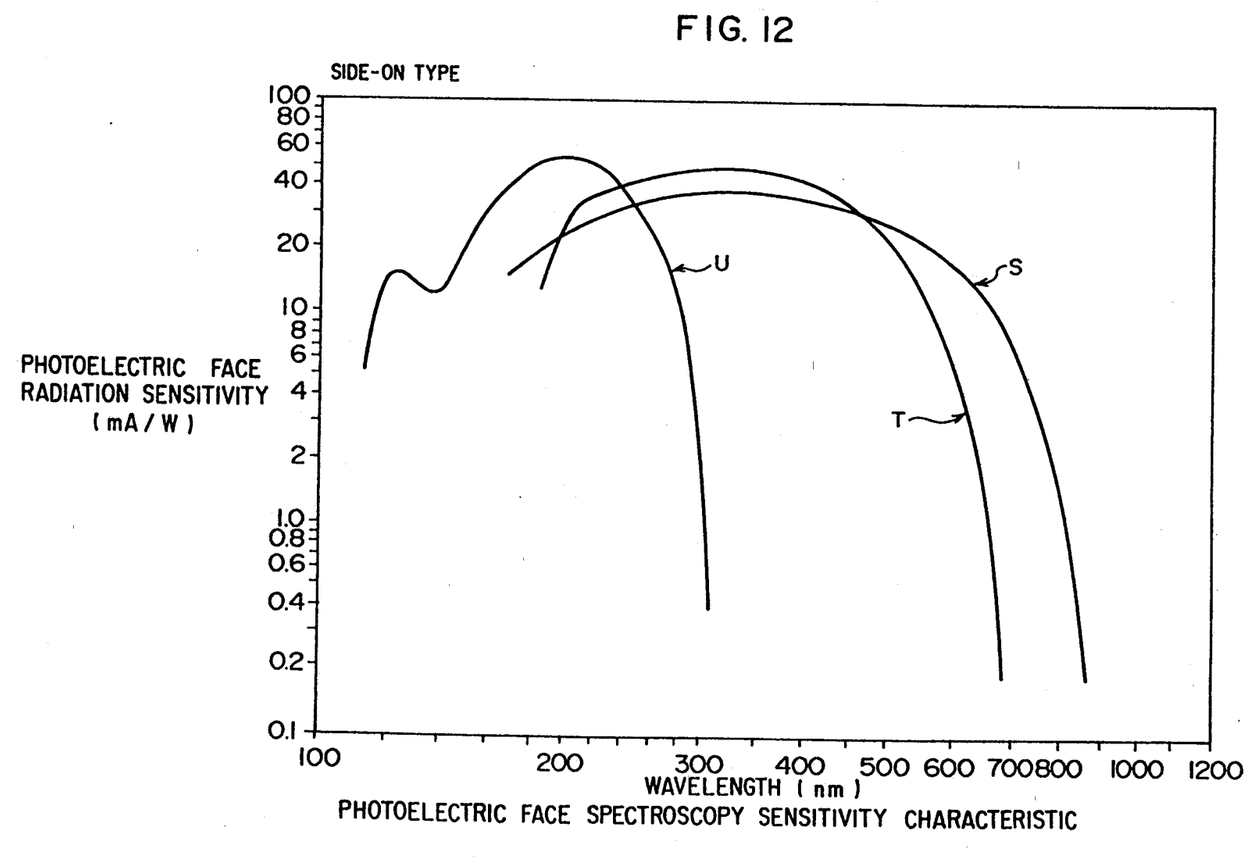
FIG. 12 illustrates the sensitivity vs. wavelength characteristic of each of various photomultipliers.

(3) Also, although photomultipliers each comprising a detector are disposed independently in the corresponding optical systems, they are the same in specifications. Therefore, they have not necessarily suitable for the atomic absorption/wavelengths of some elements to be measured and do not provide enough sensitivity. FIG. 12 shows the sensitivity vs. wavelength characteristics of photomultipliers. The characteristic of the photomultiplier varies depending on the kind of the materials constituting its photoelectric face. All the detectors are fixed to cover the same wavelength range of 190–860 nm serving as an atomic absorption spectroscopy photometer. About half of all the elements have an atomic absorption wavelength of less than 250 nm. If a photomultiplier having a sensitivity characteristic more suitable for a wavelength or element to be measured can be selected, the sensitivity will be improved greatly.

As just described above, although the conventional atomic absorption spectroscopy photometers for multi-element simultaneous analysis have various optimal device conditions such as the slit widths of the spectroscope, the blaze wavelengths of the diffraction gratings, the wavelength characteristics of the detectors, etc., due to atomic absorption wavelengths, they have not taken those conditions into consideration and hence have not derived sufficient device performances.

SUMMARY OF THE INVENTION

It is a first object of the present invention to provide a multi-element simultaneous analysis atomic absorption spectroscopy photometer which is capable of simultaneously analyzing with high sensitivity a plurality of elements to be measured simultaneously.

It is a second object of the present invention to provide a multi-element simultaneous analysis atomic absorption spectroscopy photometer which is capable of simultaneously analyzing with high sensitivity any combination of some of multiple elements simultaneously.

It is a third object of the present invention to provide a multi-element simultaneous analysis method which automatically sets device conditions of an atomic absorption spectroscopy photometer in accordance with the kinds of elements to be measured simultaneously.

A first feature of the present invention lies in a multi-element simultaneous analysis atomic absorption spectroscopy photometer which selects using a spectroscope the wavelengths of a plurality of light beams passing along a plurality of optical axes through a sample atomizing unit and simultaneously analyzes the elements contained in the sample, wherein the spectroscopes has a plurality of incident slits or exit slits or both independent of the plurality of optical axes passing through the sample atomizing unit.

A second feature of the present invention lies in that the widths of the incident slits or exit slits are variable or different from each other.

A third feature of the present invention lies in that the widths of the incident slits or exit slits are variable automatically in accordance with the kinds of elements to be measured simultaneously or that optical axes (optical systems) suitable for elements to be measured are selected automatically.

Other objects and features of the present invention will be described in detail with respect to an embodiment to be described hereinafter.

DESCRIPTION OF THE PREFERRED EMBODIMENT

Respective optical axes of a plurality of optical systems of a multi-element simultaneous analysis atomic absorption spectroscopy photometer according to the present invention only pass through a common portion of an atomizing unit. The respective optical axes of the optical systems pass through optical sources, spectroscopes, photodetectors and independent slits. Therefore, the characteristics, measuring conditions, etc., of the respective optical systems can be set for the corresponding elements to be measured simultaneously and the respective elements measured simultaneously are analyzed with high sensitivity.

Since the respective optical systems are independent of each other, means may be provided for selecting the slit width, the blaze wavelength of the diffraction grating and the kind of the photodetector for each optical system such that an optical system suitable for each element to be measured is constituted.

By setting a different slit width, different blaze wavelength, etc., beforehand in the respective optical systems and selecting an optical system suitable for an element to be measured, high-sensitivity measurement is achieved. Namely, when the respective optical systems are characterized by beforehand fixed slit widths and diffraction gratings, etc., for elements which are very frequently measured simultaneously, a special-purpose multi-element simultaneous analysis atomic spectroscopy photometer intended to be used in a special field is obtained.

Figure 1:
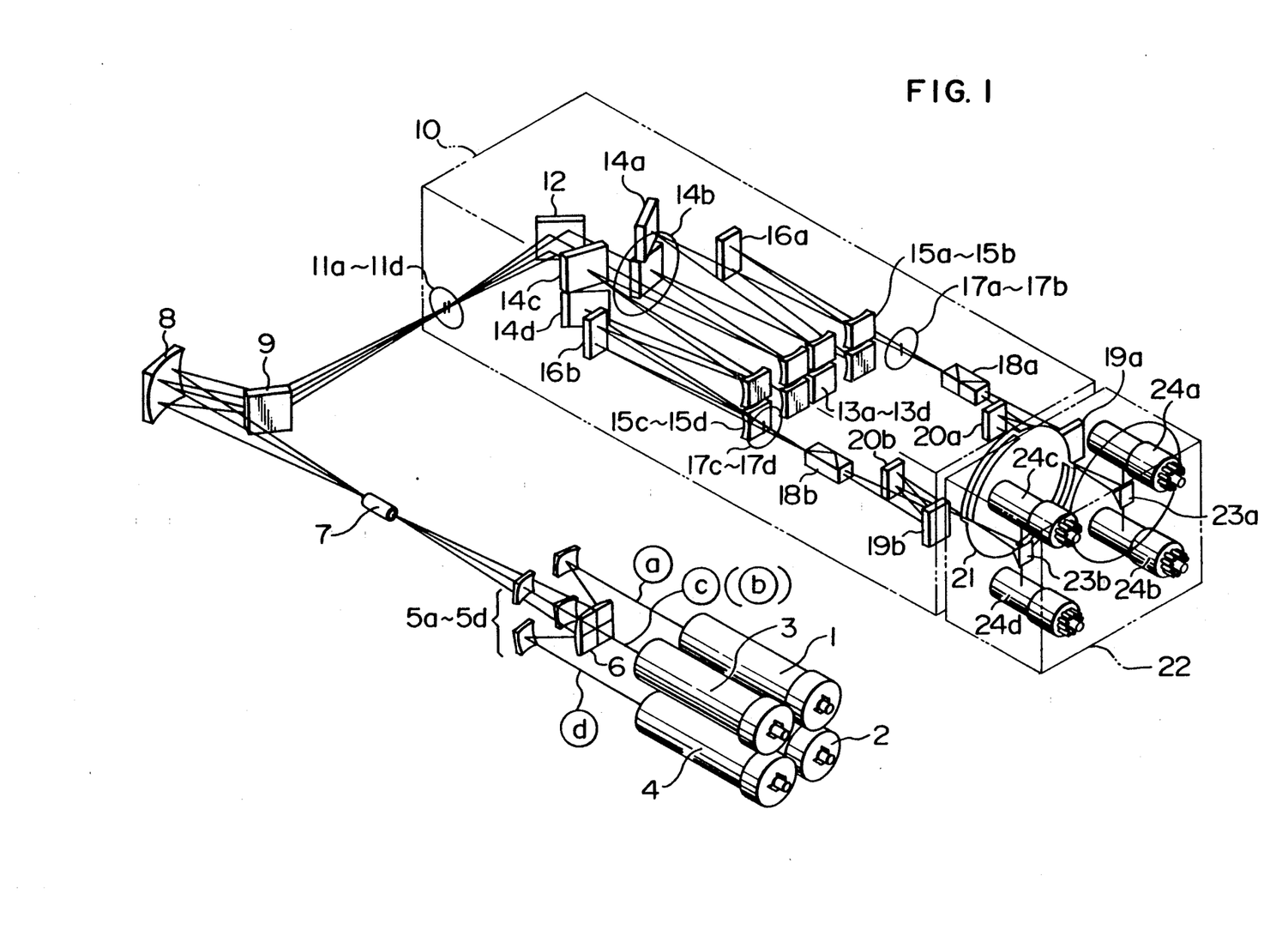
FIG. 1 illustrates an optical system of the entire multi-element simultaneous analysis atomic absorption spectroscopy photometer as one embodiment of the present invention.

One embodiment of the present invention will be described hereinafter with reference to the drawings. FIG. 1 illustrates an optical system of an atomic absorption spectroscopy photometer for 4-element simultaneous analysis. The photometer has four optical axes (a), (b), (c) and (d) ((b) and (c) are drawn superimposed). Light beams from hollow cathode lamps 1, 2, 3 and 4 disposed on the corresponding optical axes are collected by spherical mirrors 5a–5d and 6 into a cylindrical graphite cuvette 7 serving as an atomizing furnace and then led to a spectroscope 10 by a spherical mirror 8 and an additional plane mirror 9 for reducing the off-axis angle to eliminate aberration. The light beams led to the spectroscope 10 enter incident slits 11a–11d, are reflected by a plane mirror 12 to become four independent light beams and collimated by collimatirs 13a–13d, dispersed by the corresponding diffraction gratings 14a–14d, guided by camera mirrors 15a–15d and folding mirrors 16a, 16b to pass through exiting slits 17a–17d and pass through Wollaston prisms 18a, 18b at which time the light beams are divided into horizontal and vertical vibrating waves or a sample and a reference light beam in a background correcting method by the polarizing Zeeman method, and then guided by spherical mirrors 19a, 19b and plane mirrors 20a, 20b to a detector 22. The sample and reference light beams discriminated by a chopper 21 are detected by roof-like reflective mirrors 23a, 23b and photomultipliers 24a–24d and processed as electrical signals. The light beams from the hollow cathode lamps 1–4 corresponding to target elements are absorbed depending on the respective contents of elements contained in the atomic vapors of a sample when they pass through the graphite cuvette 7. The atomic absorption wavelengths inherent to the respective elements are selected by the diffraction gratings 14a–14d of the spectroscope 10, and detected by the photomultipliers 24a–24d in the detector 22 and the respective densities of the target elements are obtained from the corresponding absorbed quantities. The slits, diffraction gratings and detectors will be described hereinafter with reference to their detailed views.

Figure 2:
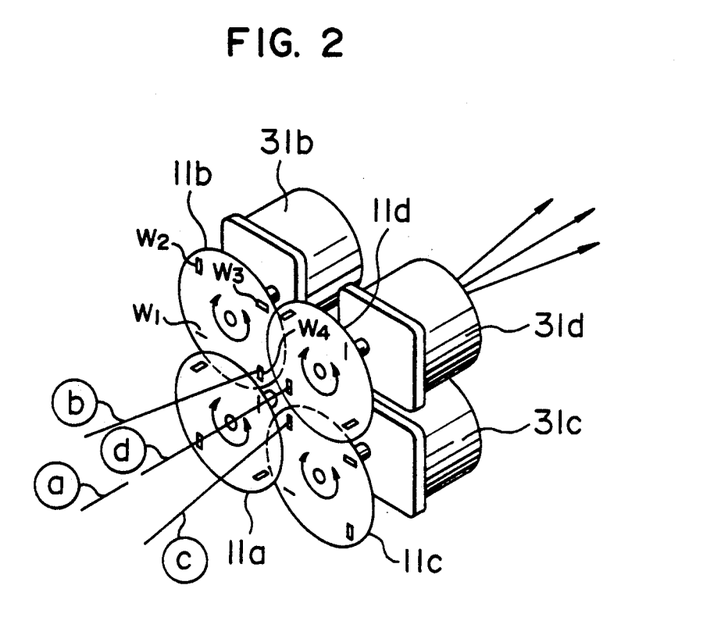
FIG. 2 illustrates an incident slit selecting mechanism according to the present invention.
Figure 3:
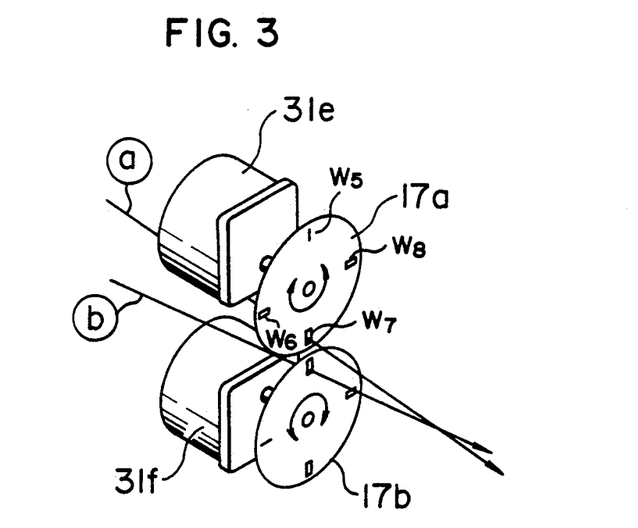
FIG. 3 illustrates an exit slit selecting mechanism according to the present invention.

FIG. 2 shows the details of the incident slits, and FIG. 3 the details of the exit slits. The incident slits $W_1$–$W_4$ and exit slits $W_5$–$W_8$ are different in width and provided in each of discs 11a–11d, and each of discs 17a–17d rotated by corresponding motors 31a–31d and 31e–31h, respectively. Appropriate slits having widths suitable for the respective elements to be measured are disposed on the optical axes (a)-(d) such that incident slits and exit slits disposed on the same optical axes have slit widths equal to each other. The respective discs 11a-11d 17a-17d are rotated through the corresponding predetermined angles from their initial positions to targeted slit widths using photocouplers, etc.

Figure 4:
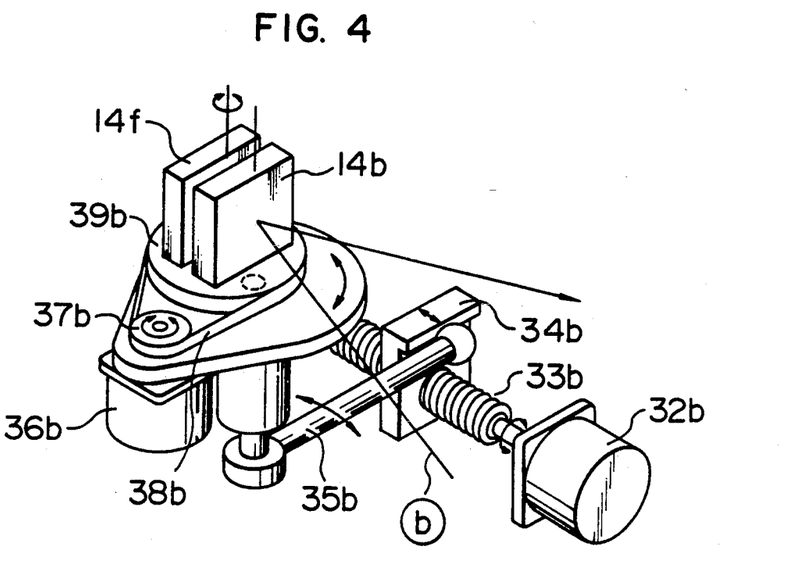
FIG. 4 illustrates a diffraction grating selecting mechanism according to the present invention.

FIG. 4 shows the details of one of the four diffraction gratings. By a command to set an atomic absorption wavelength for an element, a feed screw 33b is rotated by a motor 32b so as to move a slider 34b in the direction of the feed screw axis and to rotate a sign bar 35b in contact with the slider to thereby rotate a diffraction grating 14b through a predetermined angle, and thus a wavelength is selected such that a light beam having a target wavelength for the optical axis (b) passes through a camera mirror and then through an exit slit. When the diffraction grating 14b is for a short wavelength blaze having high diffraction efficiency on the short wavelength side, a diffraction grating 14f for a long wavelength blaze having high diffraction efficiency on the long wavelength side is provided in back-to-back relation to the diffraction grating 14b. When the atomic absorption wavelength of an element is on the long wavelength side, a pulley 39b is rotated through an angle of 180 degrees by the motor 36b through a pulley 37b and a belt 38b to thereby select and dispose the diffraction grating 14f on the optical axis. The positional relationship between the two diffraction gratings is adjusted beforehand such that the selected wavelength does not differ from the last one.

Figure 5:
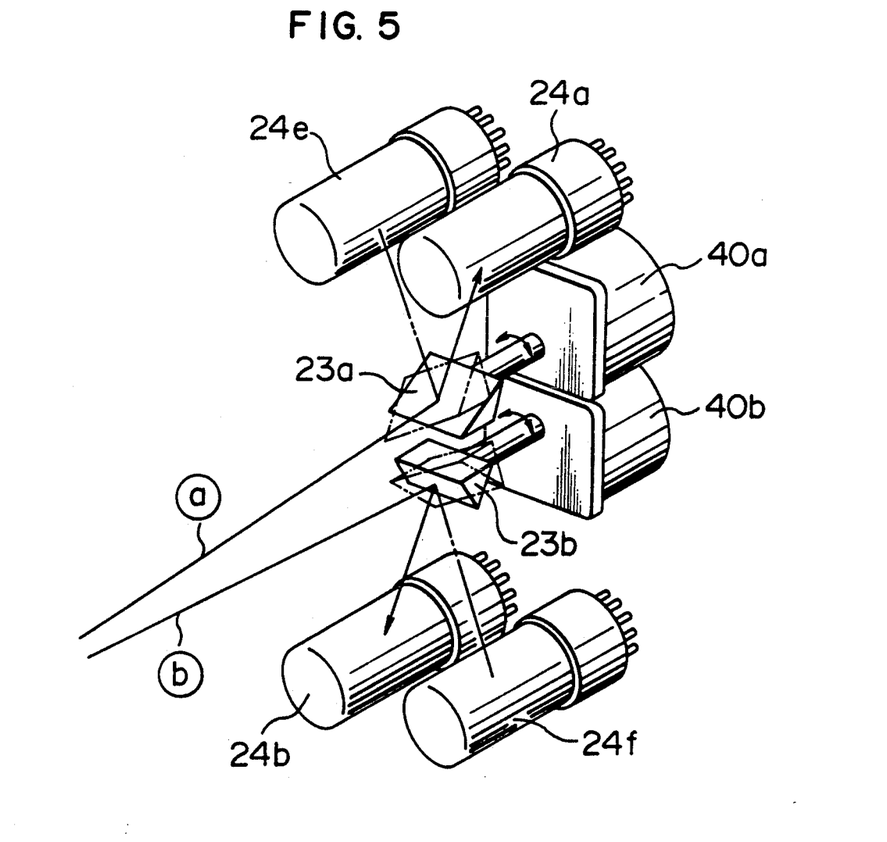
FIG. 5 illustrates a photomultiplier selecting mechanism according to the present invention.

FIG. 5 shows the details of one of two sets of detectors. The sample and reference light beams into which the (a) and (b) light beams the wavelengths of which are selected by the spectroscope are separated by the Wollaston prisms and chopper are reflected by the roof-like reflective mirrors 23a and 23b which are rotatable through a predetermined angle by motors 40a and 40b and led to photomultipliers 24a and 24b each comprising a detector, where the light beams are converted to electrical signals. The respective light beams (a) and (b), namely the respective hollow cathode lamps, turn on and off at different frequencies. The optically detected signals are processed by band-pass filters, so that the effect of one of the light beams on the other due to mixing is eliminated.

When the photomultipliers 24a and 24b each have a wavelength characteristic which covers the overall wavelength range of 190-860 nm (for a sensitivity characteristic line S of FIG. 12) in the atomic absorption spectroscopy photometer, photomultipliers 24e and 24f having different sensitivity characteristics, for example, excellent short wavelength region sensitivities (a sensitivity characteristic U of FIG. 12) may be provided adjacent the corresponding photomultipliers 24a and 24b. By rotating the reflective mirror 23a or 23b in accordance with the atomic absorption wavelength region of an element to be measured to change the light beams (a) and (b) so as to have the corresponding optical paths shown by the dot-dashed lines the sensitivity is greatly improved.

Figure 6:
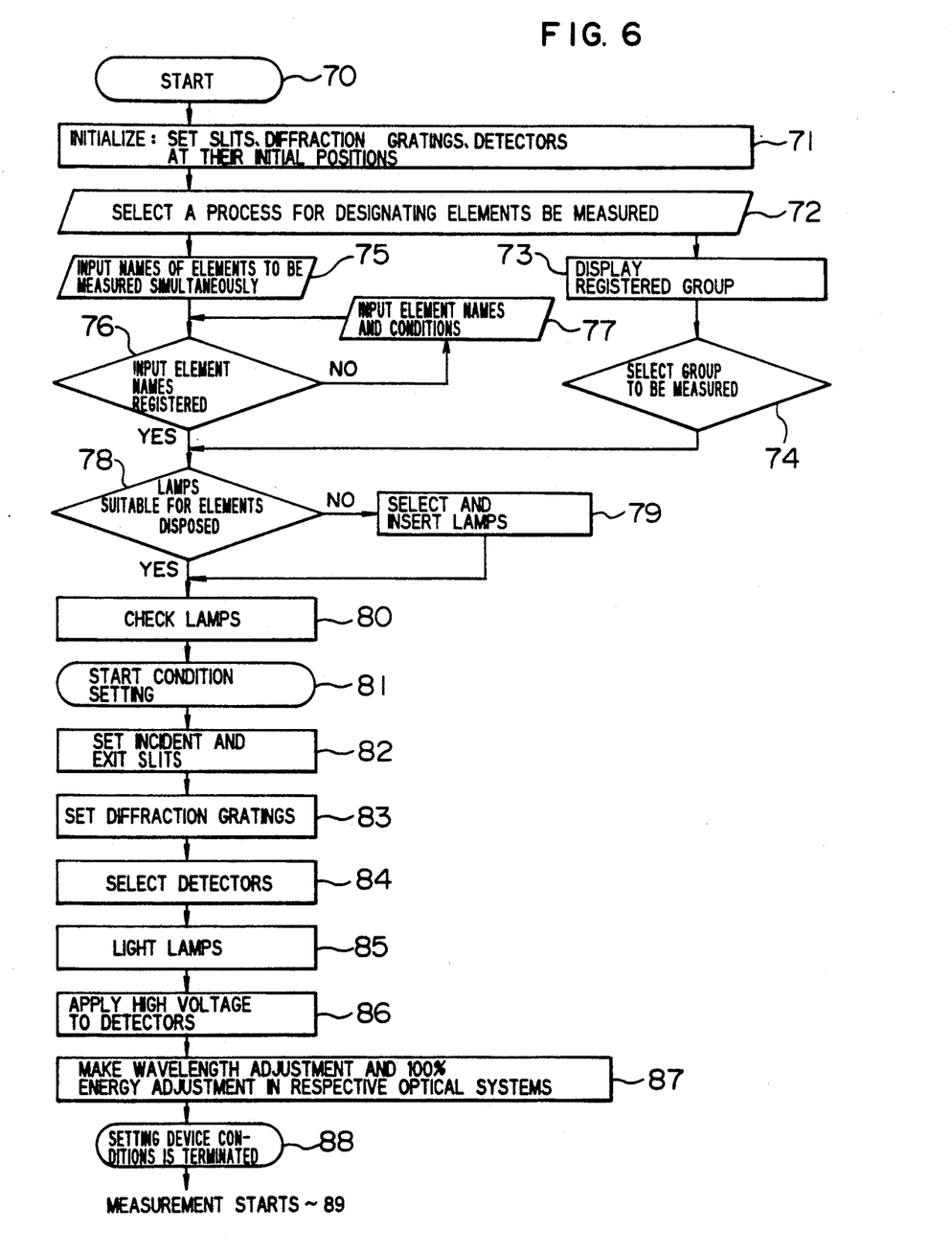
FIG. 6 is a flowchart indicative of a multielement simultaneous analysis according to one embodiment of the present invention.

A process for disposing the slit widths of the spectroscope, the diffraction gratings and the detectors, under optimal conditions for an element to be measured will be described with reference to a flowchart of FIG. 6. When the spectrometer is started by turning on its power source (step 70), the respective components, the incidence and exit slits, diffraction gratings, and detectors of the spectroscope and the position of a sample cup of an automatic sampling unit are caused to take their initial states, which is called initialization. For example, for the incident slits, the slits having the narrowest width $W_1$ are disposed on all the corresponding optical axes in FIG. 2 (step 71). A method of designating a combination of elements to be measured simultaneously is selected (step 72). If the selected combination is the same as before, it is displayed (step 73) and the group is selected (step 74). It is then checked whether hollow cathode lamps suitable for elements to be measured are disposed in the light source (step 78). When new elements are to be designated, a combination of elements to be measured simultaneously is input (step 75). It is checked by the input element names whether the conditions for the respective elements, for example, the device conditions shown in FIG. 9, the atomizing temperatures and the lamp current values are already registered (step 76). If not, or if the registered values are to be changed, new values are input (step 77). It is then checked whether the hollow cathode lamps suitable for the combination of elements to be measured are disposed in the light source (step 78). Some lamps are then replaced with required ones (step 79), it is checked whether replacement has correctly completed (step 80) and the setting of conditions is started on the basis of the optimal conditions of FIG. 9 for the respective optical systems (step 81). The incident and exit slits are adjusted to the optimal slit widths.

Assume, for example in FIG. 2, that the slit discs 11a-11d have slits $W_1$-$W_4$ which have widths of 0.2, 0.4, 0.8 and 1.3 nm corresponding to the wavelengths, that the combined elements to be measured are arsenic, selenium, iron and sodium, and that the optical axes corresponding to those elements are (a), (b), (c) and (d). In this case, $W_4$ is disposed on the optical axes (a) and (b), $W_1$ as the initial value is disposed on the optical axis (c) and $W_3$ is disposed on the optical axis (step 82). Simultaneously, the corresponding diffraction gratings are set.

For example, assume in FIG. 4 that the diffraction gratings 14b and 14f have diffraction light efficiency characteristics P (for a short wavelength region) and Q (for a long wavelength), respectively, of FIG. 11 and that the initial position is on the P side. Since the atomic absorption wavelengths of arsenic, selenium and iron of the above elements belong to the short wavelength region, the diffraction gratings corresponding to the optical axes (a), (b) and (c) are maintained on the P side, and only the diffraction grating corresponding to the optical axis (d) of sodium belonging to an intermediate wavelength region is rotated through an angle of 180 degrees to dispose a Q diffraction grating (step 83). Similarly, a detector is selected in accordance with an atomic absorption wavelength. For example, in FIG. 5, when the photomultipliers 24a and 24e or 24b and 24f have the photoelectric plane spectroscopy sensitivity characteristics S and U for the overall wavelength region and short wavelength region, respectively, in FIG. 12, the reflective mirrors corresponding to the optical axes (a), (b) and (c) are changed so as to guide light beams to the photomultiplier side from their initial position where the reflective mirrors 23a and 23b are directed so as to guide light to the S side because the atomic absorption wavelengths of arsenic, selenium and iron belong to the shorter wavelength region and sodium belongs to the intermediate wavelength region, as mentioned above (step 84).

Predetermined electric currents are then fed to the hollow cathode lamps for lighting (step 85). When the lighting is stabilized after a while, a predetermined high voltage is also applied to the respective photomultipliers on the selected optical axes in order to prepare for the next wavelength setting (step 86). The set slit widths, diffraction gratings and detectors are used for the respective optical axes, the respective wavelengths of the spectroscope are scanned to set the corresponding atomic absorption wavelengths, the voltages applied to the photomultipliers which are each a detector are adjusted so as to make a 100% energy adjustment (step 87). These steps are for preparing for the setting of the optimal device conditions suitable for the combined elements. Preparation of the automatic sampling mechanism, and confirmation of gas, water and various interlocking functions are performed concurrently to thereby complete the preparatory operations (step 88). Then the sample is measured.

Appropriate ones of the slit widths, diffraction gratings and detectors of the spectroscope have been described as being selected for each of the four optical systems. If the elements to be measured and the sensitivity levels to be required can be predicted in the field of utilization, for example, in the field of semiconductors, city water management, foods or medical use, slit widths, diffraction gratings and detectors suitable for the elements to be measured simultaneously may be provided in a fixed manner or in a combination of fixed and variable manners in the respective optical systems in conformity with their respective specifications. One of the optical systems may be for a short wavelength region and another for a long wavelength region—various combinations are possible.

Figure 7:
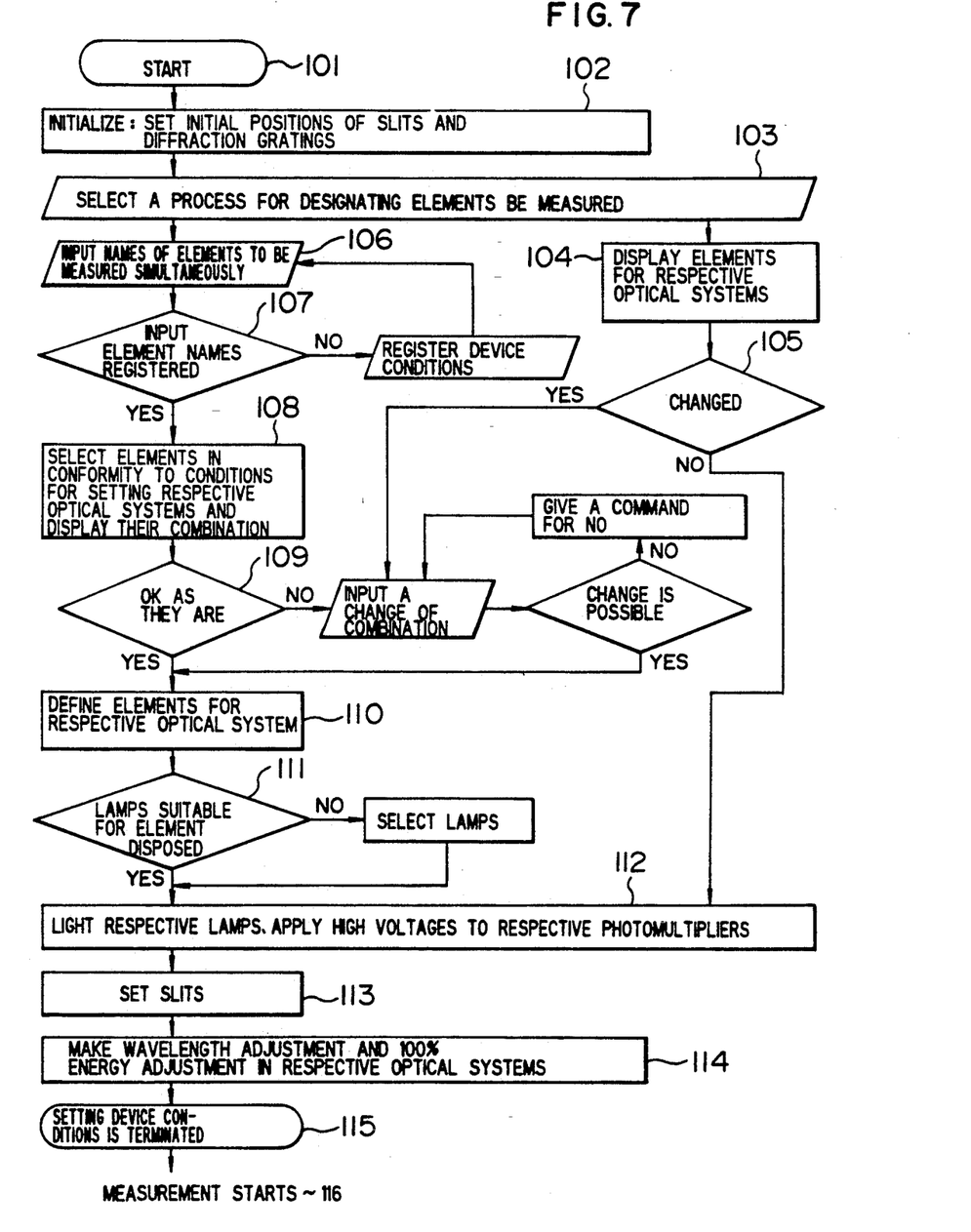
FIG. 7 is a flowchart indicative of a multielement simultaneous analysis according to another embodiment.

The respective special-purpose optical systems are provided, elements to be measured must be disposed in conformity to the respective optical systems. FIG. 7 is a flowchart indicative of a process for selecting and disposing those elements for the corresponding optical systems. This example shows that all the slits in the optical systems are variable and that one or both of diffraction gratings and detectors of some optical systems are provided for short wavelength use. When the photometer is started by turning on the power source (step 101), the respective component, slits and wavelength feed mechanisms are set to their respective initial states, which is called initialization (step 102). A process for designating elements to be measured is then selected (step 103). If the selected process is the same as before (step 104), this fact is displayed (step 104), confirmation is only made (step 105) and conditions are set (step 112). If elements are to be designated, the names of the elements to be measured simultaneously are input (step 106). It is then checked whether the atomic absorption wavelengths, slit widths, lamp currents which are the device conditions for those elements are registered (step 107). It is then determined from the atomic absorption wavelengths which optical systems those elements belong to (step 108). After the measurer confirms it (step 109), he fixes the relationship between the respective optical systems and elements (step 110) and the device conditions are set. First, it is checked whether the hollow cathode lamps for the elements to be measured are disposed in the corresponding optical systems (step 111). The predetermined electric currents are fed to the respective lamps to light same, and predetermined high voltages are applied to the photomultipliers in preparation for wavelength setting (step 112). Slits suitable for the respective elements are set in the corresponding optical systems (step 113), respective wavelength adjustments are made in the spectroscope using the lamp light beams to make a 100% energy adjustment (step 114). Thus, the setting of the device conditions related to the present invention is terminated (step 115). If setting other conditions, for example, for setting conditions for automatic samplers and heating conditions for the atomizing furnace, performed in a concurrent manner, is terminated, measurement starts.

Figure 13:
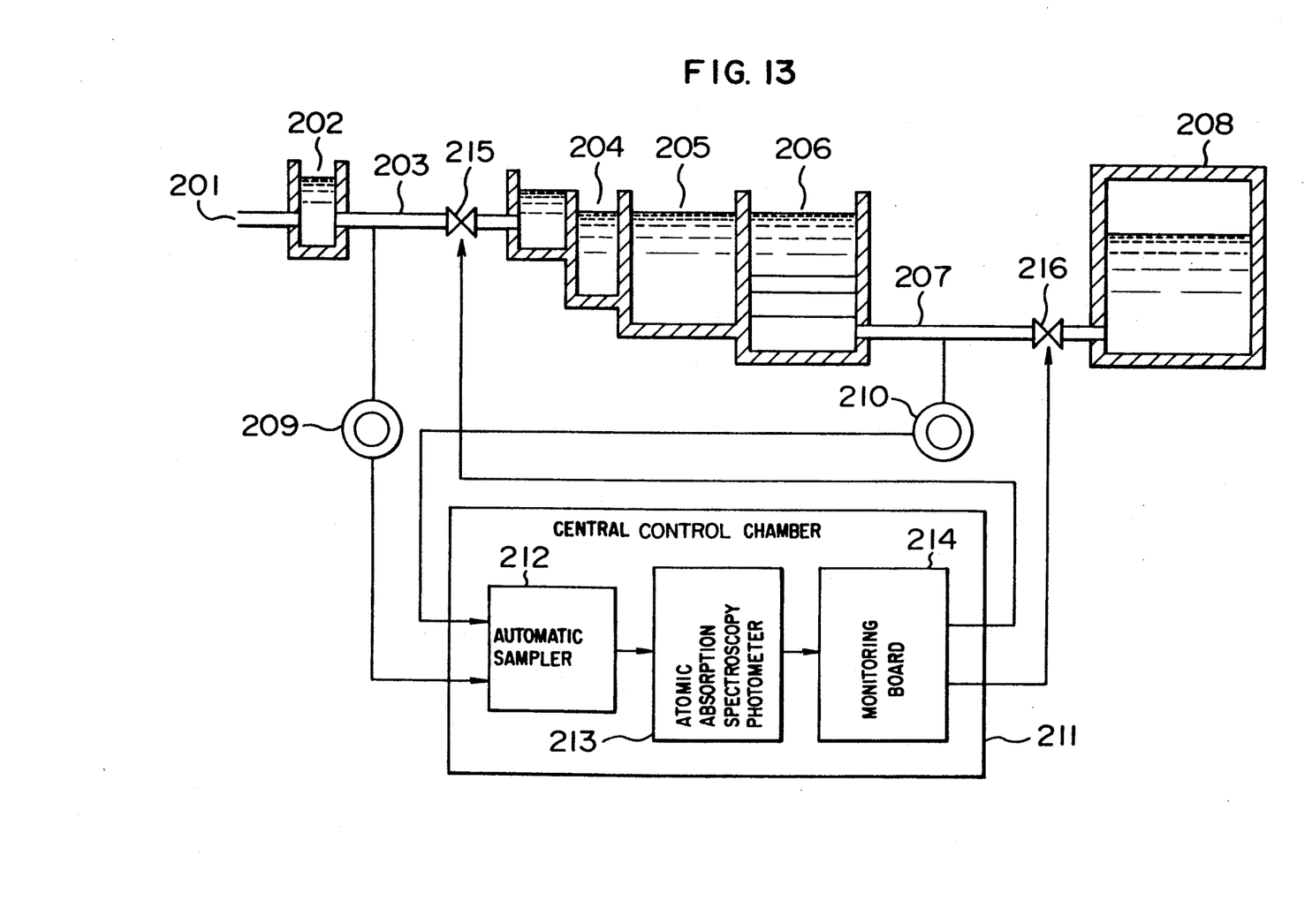
FIG. 13 illustrates one embodiment in which a multi-element simultaneous analysis atomic absorption spectroscopy photometer according to the present invention is applied to a cleaning-bed controlling system.

A city water control system and more particularly a control system for a filtration plant to which the present invention is specifically applied will be described with reference to FIG. 13.

Generally, in a filtration plant, water is taken through a reception port 201 into a well 202 and purified through a conduit 203 by a medicine injection chamber 204, a precipitation pond 205, and a filtering pond 206 to provide clean water which is then stored in a distributing reservoir 208 through a feed pipe 207.

In the filtration plant, the quality of water at the reception port 201 and the feed pipe 207 should be examined to eliminate the mixing of harmful substances into the city water. FIG. 13 shows a water examining device to which the inventive photometer is applied. In this case, water at the reception port 201 is sampled by a sampling pump 209, and water from the feed pipe 207 is also sampled by a sampling pump 210 and then the sampled water is fed to a central control chamber 211 where the sampled water from the reception port 201 and the feed pipe 207 is extracted by an automatic sampler 212 and then fed to the photometer 213 for analyzing purposes. The result of the analysis is displayed on a monitoring board 214. If harmful elements (aluminum, mercury, etc.) which exceed a prescribed value are determined to be contained, a water reception valve 215 or a water feed valve 216 is closed.

Thus, the safety of the quality of water in the clean water pipe is maintained. Thus, according to the present invention, the analytic sensitivity and speed for many harmful elements are improved greatly to thereby ensure a higher safety of the quality of water.

As described above, according to the present invention, optical systems suitable for the respective ones of combined elements to be simultaneously measured are formed individually. Slit widths in the spectroscope, wavelength characteristics for the blaze wavelengths of the diffraction gratings and wavelength characteristics of the photomultipliers each comprising a detector in the respective optical systems can be automatically selected in accordance with elements to be measured and special-purpose optical systems may be selected beforehand in accordance with the purpose of measurement. Thus the respective analytic sensitivities for elements to be measured simultaneously are improved.

We claim:

1. A control system for a filtration plant for purifying water from a reception port, and feeding the water, comprising means for sampling the fed water, a sample atomizing unit for evaporating the sampled water, and a plurality of separate optical systems using said atomizing unit in common, a plurality of photodetectors for detecting light beams having passed through said atomizing unit in the corresponding optical systems, and means for stopping feeding of the water when one of said photodetectors detects a quantity of a particular element exceeding a prescribed value.

2. A multi-element simultaneous analysis atomic absorption spectroscopy photometer comprising:

a sample atomizing unit for atomizing a sample including a plurality of elements;

means for defining a plurality of optical axes passing through the sample atomizing unit;

a plurality of light sources respectively disposed on the plurality of optical axes;

spectroscope means disposed on the plurality of optical axes for performing spectral processing of light from the plurality of light sources exiting from the sample atomizing unit;

a plurality of incident slits respectively disposed on the plurality of optical axes between the sample atomizing unit and the spectroscope means;

detecting means disposed on the plurality of optical axes for detecting spectrally processed light exiting from the spectroscope means;

a plurality of exit slits respectively disposed on the plurality of optical axes between the spectroscope means and the detecting means; and means for determining an amount of each of the plurality of elements in the sample atomized in the sample atomizing unit based on the spectrally processed light detected by the detecting means;

wherein ones of the incident slits and the exit slits disposed on same ones of the optical axes have slit widths equal to each other.

3. A multi-element simultaneous analysis atomic absorption spectroscopy photometer according to claim 2, further comprising means for varying the slit widths of the incident slits and the exit slits.

4. A water quality control system for a filtration plant, the filtration plant receiving water at a reception port, purifying the received water, and feeding the purified water, the water quality control system comprising:

means for obtaining samples of the received water, the purified water, and the fed water, the samples each including a plurality of elements;

a multi-element simultaneous analysis atomic absorption spectroscopy photometer according to claim 2 for atomizing the samples obtained by the sample obtaining means and determining an amount of each of the plurality of elements in the atomized samples;

means for determining if the samples obtained by the sample obtaining means include an amount of a predetermined one of the plurality of elements not less than a predetermined amount based on the amount of each of the plurality of elements in the atomized samples determined by the multi-element simultaneous analysis atomic absorption spectroscopy photometer; and means for generating an alarm signal when the determining means determines that the samples obtained by the sample obtaining means include an amount of the predetermined one of the plurality of elements not less than the predetermined amount.

5. A multi-element simultaneous analysis atomic absorption spectroscopy photometer comprising:

a sample atomizing unit for atomizing a sample including a plurality of elements;

means for defining a plurality of optical axes passing through the sample atomizing unit;

a plurality of light sources respectively disposed on the plurality of optical axes;

a plurality of spectroscope means respectively disposed on the plurality of optical axes for respectively performing spectral processing of light from the plurality of light sources exiting from the sample atomizing unit;

detecting means disposed on the plurality of optical axes for detecting spectrally processed light exiting from the plurality of spectroscope means; and means for determining an amount of each of the plurality of elements in the sample atomized in the sample atomizing unit based on the spectrally processed light detected by the detecting means;

wherein at least one of the plurality of spectroscope means has a spectral processing characteristic different from spectral processing characteristics of remaining ones of the plurality of spectroscope means;

said multi-element simultaneous analysis atomic absorption spectroscopy photometer further comprising:

a plurality of incident slits respectively disposed on the plurality of optical axes between the sample atomizing unit and the plurality of spectroscope means; and a plurality of exit slits respectively disposed on the plurality of optical axes between the plurality of spectroscope means and the detecting means;

wherein ones of the incident slits and the exit slits disposed on same ones of the optical axes have slit widths equal to each other.

6. A multi-element simultaneous analysis atomic absorption spectroscopy photometer according to claim 5, further comprising:

means for varying the spectral processing characteristics of the plurality of spectroscope means; and means for varying the slit widths of the incident slits and the exit slits.

7. A multi-element simultaneous analysis atomic absorption spectroscopy photometer comprising:

a sample atomizing unit for atomizing a sample including a plurality of elements;

means for defining a plurality of optical axes passing through the sample atomizing unit;

a plurality of light sources respectively disposed on the plurality of optical axes;

a plurality of spectroscope means respectively disposed on the plurality of optical axes for respectively performing spectral processing of light from the plurality of light sources exiting from the sample atomizing unit;

detecting means disposed on the plurality of optical axes for detecting spectrally processed light exiting from the plurality of spectroscope means; and means for determining an amount of each of the plurality of elements in the sample atomized in the sample atomizing unit based on the spectrally processed light detected by the detecting means;

wherein at least one of the plurality of spectroscope means has a spectral processing characteristic different from spectral processing characteristics of remaining ones of the plurality of spectroscope means; and wherein at least one of the plurality of spectroscope means includes:

a plurality of diffraction gratings having mutually different spectral characteristics; and means for disposing a selected one of the plurality of diffraction gratings on one of the plurality of optical axes on which the at least one spectroscope means is disposed.

8. A multi-element simultaneous analysis atomic absorption spectroscopy photometer comprising:
   a sample atomizing unit for atomizing a sample including a plurality of elements;
   means for defining a plurality of optical axes passing through the sample atomizing unit;
   a plurality of light sources respectively disposed on the plurality of optical axes;
   spectroscope means disposed on the plurality of optical axes for performing spectral processing of light from the plurality of light sources exiting from the sample atomizing unit;
   a plurality of detecting means respectively disposed on the plurality of optical axes for detecting spectrally processed light exiting from the spectroscope means; and
   means for determining an amount of each of the plurality of elements in the sample atomized in the sample atomizing unit based on the spectrally processed light detected by the plurality of detecting means;
   wherein at least one of the plurality of detecting means has a detecting characteristic different from detecting characteristics of remaining ones of the plurality of detecting means;
   said multi-element simultaneous analysis atomic absorption spectroscopy photometer further comprising:
   a plurality of incident slits respectively disposed on the plurality of optical axes between the sample atomizing unit and the spectroscope means; and
   a plurality of exit slits respectively disposed on the plurality of optical axes between the spectroscope means and the plurality of detecting means;
   wherein ones of the incident slits and the exit slits disposed on same ones of the optical axes have slit widths equal to each other.

9. A multi-element simultaneous analysis atomic absorption spectroscopy photometer according to claim 8, further comprising:
   means for varying the detecting characteristics of the plurality of detecting means; and
   means for varying the slit widths of the incident slits and the exit slits.

10. A multi-element simultaneous analysis atomic absorption spectroscopy photometer comprising:
    a sample atomizing unit for atomizing a sample including a plurality of elements;
    means for defining a plurality of optical axes passing through the sample atomizing unit;
    a plurality of light sources respectively disposed on the plurality of optical axes;
    a plurality of spectroscope means respectively disposed on the plurality of optical axes for respectively performing spectral processing of light from the plurality of light sources exiting from the sample atomizing unit;
    a plurality of incident slits respectively disposed on the plurality of optical axes between the sample atomizing unit and the plurality of spectroscope means;
    a plurality of detecting means respectively disposed on the plurality of optical axes for respectively detecting spectrally processed light exiting from the plurality of spectroscope means;
    a plurality of exit slits respectively disposed on the plurality of optical axes between the plurality of spectroscope means and the plurality of detecting means; and
    means for determining an amount of each of the plurality of elements in the sample atomized in the sample atomizing unit based on the spectrally processed light detected by the plurality of detecting means;
    wherein at least one of the plurality of spectroscope means has a spectral processing characteristic different from spectral processing characteristics of remaining ones of the plurality of spectroscope means;
    wherein at least one of the plurality of detecting means has a detecting characteristic different from detecting characteristics of remaining ones of the plurality of detecting means; and
    wherein ones of the incident slits and the exit slits disposed on same ones of the optical axes have slit widths equal to each other.

11. A multi-element simultaneous analysis atomic absorption spectroscopy photometer according to claim 10, further comprising:
    means for varying the spectral processing characteristics of the plurality of spectroscope means;
    means for varying the detecting characteristics of the plurality of detecting means; and
    means for varying the slit widths of the incident slits and the exit slits.

12. A water quality control system for a filtration plant, the filtration plant receiving water at a reception port, purifying the received water, and feeding the purified water, the water quality control system comprising:
    means for obtaining samples of the received water, the purified water, and the fed water, the samples each including a plurality of elements;
    a multi-element simultaneous analysis atomic absorption spectroscopy photometer according to claim 10 for atomizing the samples obtained by the sample obtaining means and determining an amount of each of the plurality of elements in the atomized samples;
    means for determining if the samples obtained by the sample obtaining means include an amount of a predetermined one of the plurality of elements not less than a predetermined amount based on the amount of each of the plurality of elements in the atomized samples determined by the multi-element simultaneous analysis atomic absorption spectroscopy photometer; and
    means for generating an alarm signal when the determining means determines that the samples obtained by the sample obtaining means include an amount of the predetermined one of the plurality of elements not less than the predetermined amount.

13. An atomic absorption analysis method for simultaneously analyzing a plurality of elements, comprising the steps of:
    atomizing a sample including a plurality of elements;
    directing light from a plurality of light sources along a respective plurality of optical axes extending through the atomized sample;
    disposing spectroscope means on the plurality of optical axes to receive light from the plurality of light sources exiting from the atomized sample;

respectively disposing a plurality of incident slits on the plurality of optical axes between the atomized sample and the spectroscope means;

performing spectral processing of the light from the plurality of light sources exiting from the atomized sample with the spectroscope means;

disposing detecting means on the plurality of optical axes to receive spectrally processed light exiting from the spectroscope means;

respectively disposing a plurality of exit slits on the plurality of optical axes between the spectroscope means and the detecting means;

detecting the spectrally processed light exiting from the spectroscope means with the detecting means; and determining an amount of each of the plurality of elements in the atomized sample based on the spectrally processed light detected by the detecting means;

wherein ones of the incident slits and the exit slits disposed on same ones of the optical axes have slit widths equal to each other.

14. An atomic absorption analysis method for simultaneously analyzing a plurality of elements according to claim 13, further comprising the step of varying the slit widths of the incident slits and the exit slits.

15. An atomic absorption analysis method for simultaneously analyzing a plurality of elements, comprising the steps of:

atomizing a sample including a plurality of elements;

directing light from a plurality of light sources along a respective plurality of optical axes extending through the atomized sample;

respectively disposing a plurality of spectroscope means on the plurality of optical axes to respectively receive light from the plurality of light sources exiting from the atomized sample, at least one of the plurality of spectroscope means having a spectral processing characteristic different from spectral processing characteristics of remaining ones of the plurality of spectroscope means;

respectively disposing a plurality of incident slits on the plurality of optical axes between the atomized sample and the plurality of spectroscope means;

respectively performing spectral processing of the light from the plurality of light sources exiting from the atomized sample with the plurality of spectroscope means;

respectively disposing a plurality of detecting means on the plurality of optical axes to respectively receive spectrally processed light exiting from the plurality of spectroscope means, at least one of the plurality of detecting means having a detecting characteristic different from detecting characteristics of remaining ones of the plurality of detecting means;

respectively disposing a plurality of exit slits on the plurality of optical axes between the plurality of spectroscope means and the plurality of detecting means;

respectively detecting the spectrally processed light exiting from the plurality of spectroscope means with the plurality of detecting means; and determining an amount of each of the plurality of elements in the atomized sample based on the spectrally processed light detected by the plurality of detecting means;

wherein ones of the incident slits and the exit slits disposed on same ones of the optical axes have slit widths equal to each other.

16. An atomic absorption analysis method for simultaneously analyzing a plurality of elements according to claim 15, further comprising the steps of:

varying the spectral processing characteristics of the plurality of spectroscope means;

varying the detecting characteristics of the plurality of detecting means; and varying the slit widths of the incident slits and the exit slits.

17. A multi-element simultaneous analysis atomic absorption spectroscopy photometer comprising:

a sample atomizing unit for atomizing a sample including a plurality of elements;

means for defining a plurality of optical axes passing through the sample atomizing unit;

a plurality of light sources respectively disposed on the plurality of optical axes;

a plurality of spectroscope means respectively disposed on the plurality of optical axes for respectively performing spectral processing of light from the plurality of light sources exiting from the sample atomizing unit;

detecting means disposed on the plurality of optical axes for detecting spectrally processed light exiting from the plurality of spectroscope means; and means for determining an amount of each of the plurality of elements in the sample atomized in the sample atomizing unit based on the spectrally processed light detected by the detecting means;

wherein at least one of the plurality of spectroscope means has a spectral processing characteristic different from spectral processing characteristics of remaining ones of the plurality of spectroscope means; and wherein the spectral processing characteristic of the at least one of the plurality of spectroscope means differs from the spectral processing characteristics of the remaining ones of the plurality of spectroscope means in at least one factor other than a selected wavelength.

18. A multi-element simultaneous analysis atomic absorption spectroscopy photometer according to claim 17, wherein the spectral processing characteristic of the at least one of the plurality of spectroscope means differs from the spectral processing characteristics of the remaining ones of the plurality of spectroscope means in a slit width of an incident slit, a slit width of an exit slit, and a blaze wavelength of a diffraction grating.

19. A multi-element simultaneous analysis atomic absorption spectroscopy photometer according to claim 17, further comprising means for varying the spectral processing characteristics of the plurality of spectroscope means.

20. A multi-element simultaneous analysis atomic absorption spectroscopy photometer according to claim 17, further comprising:

means for specifying a plurality of elements to be analyzed included in the sample; and means for varying the spectral processing characteristics of the plurality of spectroscope means in accordance with the plurality of elements specified by the specifying means.

21. A water quality control system for a filtration plant, the filtration plant receiving water at a reception port, purifying the received water, and feeding the purified water, the water quality control system comprising:

means for obtaining samples of the received water, the purified water, and the fed water, the samples each including a plurality of elements;
  a multi-element simultaneous analysis atomic absorption spectroscopy photometer according to claim 17 for atomizing the samples obtained by the sample obtaining means and determining an amount of each of the plurality of elements in the atomized samples;
  means for determining if the samples obtained by the sample obtaining means include an amount of a predetermined one of the plurality of elements not less than a predetermined amount based on the amount of each of the plurality of elements in the atomized samples determined by the multi-element simultaneous analysis atomic absorption spectroscopy photometer; and
  means for generating an alarm signal when the determining means determines that the samples obtained by the sample obtaining means include an amount of the predetermined one of the plurality of elements not less than the predetermined amount.

22. A multi-element simultaneous analysis atomic absorption spectroscopy photometer comprising:
  a sample atomizing unit for atomizing a sample including a plurality of elements;
  means for defining a plurality of optical axes passing through the sample atomizing unit;
  a plurality of light sources respectively disposed on the plurality of optical axes;
  spectroscope means disposed on the plurality of optical axes for performing spectral processing of light from the plurality of light sources exiting from the sample atomizing unit;
  a plurality of detecting means respectively disposed on the plurality of optical axes for detecting spectrally processed light exiting from the spectroscope means; and
  means for determining an amount of each of the plurality of elements in the sample atomized in the sample atomizing unit based on the spectrally processed light detected by the plurality of detecting means;
  wherein at least one of the plurality of detecting means has a detecting characteristic different from detecting characteristics of remaining ones of the plurality of detecting means; and
  wherein the detecting characteristics of the at least one of the plurality of detecting means differs from the detecting characteristics of the remaining ones of the plurality of detecting means in at least a sensitivity characteristic.

23. A multi-element simultaneous analysis atomic absorption spectroscopy photometer according to claim 22, further comprising means for varying the detecting characteristics of the plurality of detecting means.

24. A multi-element simultaneous analysis atomic absorption spectroscopy photometer according to claim 23, wherein at least one of the plurality of detecting means includes:
  a plurality of detectors having mutually different detecting characteristics; and
  means for disposing a selected one of the plurality of detectors on one of the plurality of optical axes on which the at least one detecting means is disposed.

25. A multi-element simultaneous analysis atomic absorption spectroscopy photometer according to claim 22, further comprising:
  means for specifying a plurality of elements to be analyzed included in the sample; and
  means for varying the detecting characteristics of the plurality of detecting means in accordance with the plurality of elements specified by the specifying means.

26. A water quality control system for a filtration plant, the filtration plant receiving water at a reception port, purifying the received water, and feeding the purified water, the water quality control system comprising:
  means for obtaining samples of the received water, the purified water, and the fed water, the samples each including a plurality of elements;
  a multi-element simultaneous analysis atomic absorption spectroscopy photometer according to claim 22 for atomizing the samples obtained by the sample obtaining means and determining an amount of each of the plurality of elements in the atomizing samples;
  means for determining if the samples obtained by the sample obtaining means include an amount of a predetermined one of the plurality of elements not less than a predetermined amount based on the amount of each of the plurality of elements in the atomized samples determined by the multi-element simultaneous analysis atomic absorption spectroscopy photometer; and
  means for generating an alarm signal when the determining means determines that the samples obtained by the sample obtaining means include an amount of the predetermined one of the plurality of elements not less than the predetermined amount.

27. An atomic absorption analysis method for simultaneously analyzing a plurality of elements, comprising the steps of:
  atomizing a sample including a plurality of elements;
  directing light from a plurality of light sources along a respective plurality of optical axes extending through the atomized sample;
  respectively disposing a plurality of spectroscope means on the plurality of optical axes to respectively receive light from the plurality of light sources exiting from the atomized sample, at least one of the plurality of spectroscope means having a spectral processing characteristic different from spectral processing characteristics of remaining ones of the plurality of spectroscope means;
  respectively performing spectral processing of the light from the plurality of light sources exiting from the atomized sample with the plurality of spectroscope means;
  disposing detecting means on the plurality of optical axes to receive spectrally processed light exiting from the plurality of spectroscope means;
  detecting the spectrally processed light exiting from the plurality of spectroscope means with the detecting means; and
  determining an amount of each of the plurality of elements in the atomized sample based on the spectrally processed light detected by the detecting means;
  wherein the spectral processing characteristic of the at least one of the plurality of spectroscope means differs from the spectral processing characteristics of the remaining ones of the plurality of spectroscope means in at least one factor other than a selected wavelength.

28. An atomic absorption analysis method for simultaneously analyzing a plurality of elements according to claim 27, further comprising the step of varying the spectral processing characteristics of the plurality of spectroscope means.

29. An atomic absorption analysis method for simultaneously analyzing a plurality of elements according to claim 27, further comprising the steps of:
   specifying a plurality of elements to be analyzed included in the sample; and
   varying the spectral processing characteristics of the plurality of spectroscope means in accordance with the plurality of elements specified in the specifying step.

30. An atomic absorption analysis means for simultaneously analyzing a plurality of elements, comprising the steps of:
   atomizing a sample including a plurality of elements;
   directing light from a plurality of light sources along a respective plurality of optical axes extending through the atomized sample;
   disposing spectroscope means on the plurality of optical axes to receive light from the plurality of light sources exiting from the atomized sample;
   performing spectral processing of the light from the plurality of light sources exiting from the atomized sample with the spectroscope means;
   disposing a plurality of detecting means on the plurality of optical axes to receive spectrally processed light exiting from the spectroscope means, at least one of the plurality of detecting means having a detecting characteristic different from detecting characteristics of remaining ones of the plurality of detecting means;
   detecting the spectrally processed light exiting from the spectroscope means with the plurality of detecting means; and
   determining an amount of each of the plurality of elements in the atomized sample based on the spectrally processed light detected by the plurality of detecting means;
   wherein the detecting characteristic of the at least one of the plurality of detecting means differs from the detecting characteristics of the remaining ones of the plurality of detecting means in at least a sensitivity characteristic.

31. An atomic absorption analysis method for simultaneously analyzing a plurality of elements according to claim 30, further comprising the step of varying the detecting characteristics of the plurality of detecting means.

32. An atomic absorption analysis method for simultaneously analyzing a plurality of elements according to claim 30, further comprising the steps of:
   specifying a plurality of elements to be analyzed included in the sample; and
   varying the detecting characteristics of the plurality of detecting means in accordance with the plurality of elements specified in the specifying step.

* * * * *